United States Patent [19]
Silvian

[11] Patent Number: 5,170,414
[45] Date of Patent: Dec. 8, 1992

[54] ADJUSTABLE OUTPUT LEVEL SIGNAL TRANSMITTER

[75] Inventor: Sergiu Silvian, La Crescenta, Calif.

[73] Assignee: Siemens Pacesetter, Inc., Sylmar, Calif.

[21] Appl. No.: 405,905

[22] Filed: Sep. 12, 1989

[51] Int. Cl.$^5$ ............................................. H04L 27/04
[52] U.S. Cl. ...................................... 375/59; 375/68; 331/173; 331/166; 178/116
[58] Field of Search ................ 375/68, 59; 331/172, 331/173, 174, 165, 166; 178/66.1, 116, 66.2; 128/419 P, 419 PG, 422

[56] References Cited

U.S. PATENT DOCUMENTS

| | | | |
|---|---|---|---|
| 2,815,426 | 12/1957 | Rothstein | 178/116 |
| 3,518,551 | 6/1970 | Carniol et al. | 331/166 |
| 3,866,145 | 2/1975 | Hess, Jr. et al. | 331/166 X |

*Primary Examiner*—Curtis Kuntz
*Assistant Examiner*—Tesfaldet Bocure
*Attorney, Agent, or Firm*—Malcolm J. Romano

[57] ABSTRACT

An adjustable output level transmitter includes a direct current energy source, an L-C tank circuit and a switching means for sequentially coupling the capacitors of the tank circuit to the direct current energy source and ground. The output signal frequency is equal to the resonant frequency of the L-C tank circuit and the output signal level is a function of which capacitors of the L-C tank circuit are sequentially coupled to the energy source. The circuit functions in a Class D mode with the inherent advantages of minimal power loss and very high efficiency. Due to the manner of switching utilized, the output signal frequency is very stable and unaffected by the mode of capacitor switching.

21 Claims, 1 Drawing Sheet

| CAPACITOR VALUES | CONTL1 | CONTL2 | OUTPUT LEVEL |
|---|---|---|---|
| | 0 | 0 | 0 |
| $C1 = K \cdot C$ | 1 | 0 | $K \cdot V_{MAX}$ |
| $C2 = (1-K) \cdot C$ | 0 | 1 | $(1-K) \cdot V_{MAX}$ |
| | 1 | 1 | $V_{MAX}$ |

5,170,414

ADJUSTABLE OUTPUT LEVEL SIGNAL TRANSMITTER

BACKGROUND OF THE INVENTION

The present invention relates to a variable output voltage constant-frequency transmitter, and, in particular, to a transmitter capable of providing discrete output voltage level changes without sacrificing performance, simplicity and power supply efficiency.

Prior art signal transmitter devices in common use range from those defined by Class A to Class D operation. Class A transmitters, being continuous wave operation, have the greatest level of control on output voltage variability, but suffer from poor efficiency of operation and, therefore, are wasteful of power. Class D transmitters, on the other hand, hold out the greatest promise when considering efficiency, but generally lack sufficient output level control to be practical transmitters for satisfying the requirement for controllability over a range of output voltage levels. Methods known for controlling output voltage level changes include autotransformer coupling and power supply voltage variations. These techniques, however, contribute to the complexity and loss of efficiency and, therefore, the cost and desirability of the transmitter.

An application of transmitters of the type described herein is for telemetric communication between an external control device, such as a programmer, and a pacemaker inductor coil, which is included in an implanted pacemaker to be programmed. Typically, the programming information is in the form of modulated telemetered signals from the transmitter to the pacemaker. The type of information normally transmitted is known in the art and, therefore, will not be repeated here. The physiology of the patient having the pacemaker implanted determines, to a major degree, the output level required of the transmitter in order to effectively program the pacemaker.

Normally, transmitter output signals are sinusoidal in nature, with transmitter frequencies being established by inductor-capacitor tank circuits with its resonant frequency being a function of $$\frac{1}{\sqrt{LC}}.$$

In the above equation, L represents the value of the inductance, and C represents the value of the capacitance of the tank circuit.

Illustrative of the shortcomings of conventional methods of output level control, is, for example, an autotransformer-type transmitter, where inductance changes, due to selection of different transformer taps for voltage level changes, affect the resonant frequency of the transmitter output signal. Control of power supply output voltage, on the other hand, is found to be wasteful of power.

Accordingly, to accommodate required output level changes, while avoiding the degradation of efficiency or frequency shift due to inductance value changes, the present invention provides a controllable transmitter output voltage while maintaining highly efficient frequency stable operation.

SUMMARY OF THE INVENTION

In accordance with the present invention, an adjustable output level transmitter is provided, having a direct current source of electrical energy and a parallel L-C tank circuit. The source of electrical energy and the tank circuit have a common ground. A controllable switch is located between the energy source and the tank circuit for coupling and decoupling the tank circuit and the energy source at a selected frequency.

Preferably the selected frequency is equal to the resonant frequency of the tank circuit, and the tank circuit capacitance C comprises two capacitors in series circuit connection with the inductance L connected between the capacitors and ground. Each capacitor is driven by a driver that couples the capacitor either to the energy source or to ground. In this manner, the total capacitance value of the tank circuit remains constant, as does the inductance value. Accordingly, the tank circuit resonant frequency and therefore the output voltage frequency remains substantially a constant value independent of output voltage level. The capacitors may be selected in a ratio equal to the desired ratio of the output voltage operating levels.

For maximum voltage output, both capacitors are driven synchronously, each capacitor being coupled to the output of a respective one of the drivers. For adjusting the output signal level of the transmitter to desired value, only the corresponding capacitor required to provide such desired output level is driven; the other capacitor being coupled to the common ground. In this manner, output signal levels of the transmitter are variable, while maintaining the total capacitance value of the L-C tank circuit constant. Thus, the resonant frequency of the transmitter remains constant, independent of the number and identity of the capacitors driven.

An alternating current signal generator, having a fundamental frequency essentially equal to that of the resident frequency of the L-C tank circuit, is logically coupled to the drivers. Thus, by selecting the appropriate logical control signals, either one or both of the capacitors may be driven.

Preferably, the alternating current signal source is a square-wave signal, having a 50% duty cycle and a fundamental frequency equal to the resonant frequency of the L-C tank circuit.

DETAILED DESCRIPTION

Figures 1, 2:
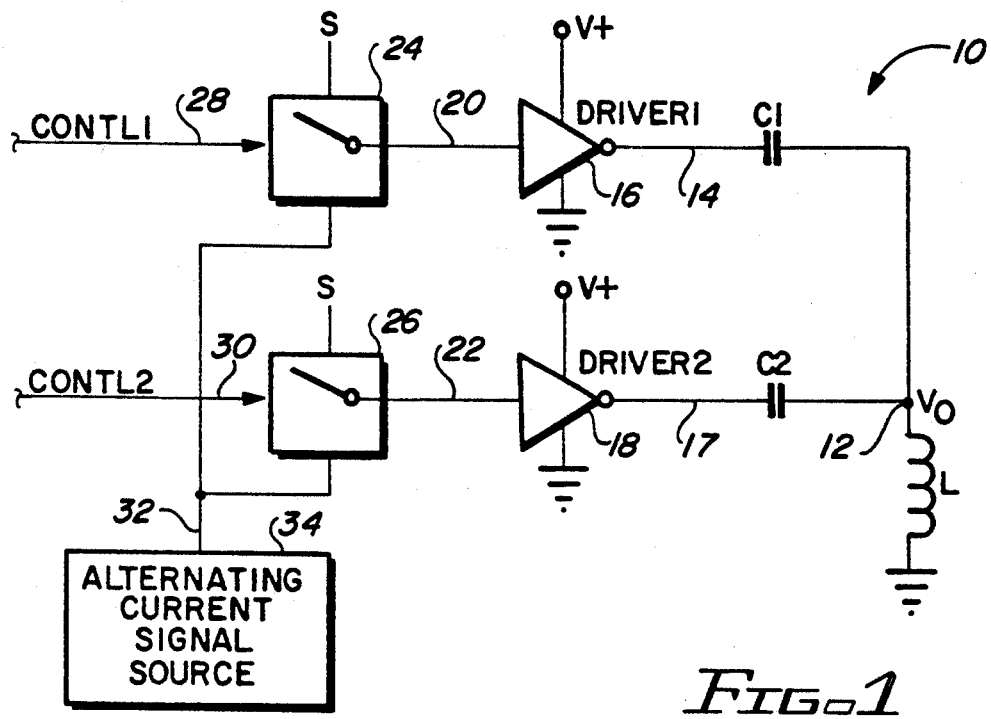
FIG. 1 is a schematic drawing of the circuit of the present invention.
FIG. 2 is a truth table relating transmitter output voltage level to logic inputs.

Referring now to FIG. 1, there is shown in schematic diagram, the circuit 10 which represents the preferred embodiment of the present invention. Circuit 10 operates electrically as a Class D transmitter. As previously described, one of the merits of using Class D transmitters is that approximately 100% of the current delivered by the source of electrical energy (V) passes through the load. The load for circuit 10 comprises the L-C tank circuit of capacitors C1, C2 and the inductor L. More specifically, capacitors C1 and C2 are connected in series circuit connection, with the point of connection 12 of C1 and C2 serving as the output terminal (V$_0$) of the adjustable level output transmitter. Capacitor C1 is coupled to the output 14 of driver 16, and capacitor C2 is coupled to the output 17 of driver 18. To complete the L-C tank circuit, the inductor L is coupled between node 12 and ground.

The L-C tank circuit load is driven by a pair of drivers 16 and 18 Each driver functions preferably as a complementary switch such that the outputs (14, 17) are coupled either to the source V or to ground, depending on the level of the input (20, 22, respectively). Accordingly, if a logical "0" appears at node 20, then the output 14 will be connected to the source V, and if a logical "1" appears at node 20, the output 14 will be connected to ground. Such devices are available as CMOS drivers manufactured by the RCA Corporation under the model designation CD4049. These devices are NMOS-PMOS series coupled CMOS transistors, each of which are rendered conductive dependent upon the value of the input signal. The choice of logical state control is arbitrary, and any consistent set of logical "values" are contemplated by the invention.

Coupled to the input 20 of driver 16 is the output of a driver control circuit 24. Similarly, the input 22 of driver 18 is coupled to the output of driver control circuit 26. Each driver control circuit (24, 26) preferably has three inputs comprising a logical input signal, a direct current signal source S, and a signal from the alternating current signal source 34. The source S may, for the sake of convenience, be the same as the source V. The logic input signal 28 identified in FIG. 1 as CONTL1 and the logic input signal 30 identified in FIG. 1 as CONTL2 preferably take on the logical values "1" and "0". In the logical "0" state, the inputs 20 and 22 are connected to source S, and in the logical "1" state, the inputs 20 and 22 are connected to the output 32 of an alternating current signal source 34.

Although other signal characteristics may be utilized, preferably the form of the alternating current signal is a square-wave having a 50% duty cycle and a magnitude swing from logical "0" to logical "1". If the drivers 16 and 18 are selected to operate under negative logic conditions, the magnitude swing may be adjusted accordingly; that is, between 0 and a negative value.

Preferably, the frequency of the source 34 is $F_0$, where $F_0$ is measured in cycles per second (hertz).

$$F_0 = \frac{1}{2\pi \sqrt{LC}}$$

where C is the value of capacitance of capacitors C1+C2 and L is the value of the inductance of the inductor L.

When logic input CONTL1 and CONTL2 are in the logical "1" state, drivers 16 and 18 are driven by the source 34, such that the output voltage $V_0$ will have its maximum value equal to $V_{max}$. The output voltage $V_0$ will also have a fundamental frequency of oscillation $F_0$ with a minimum of harmonic content.

The magnitude of the output voltage $V_0$ is changeable in discrete steps in accordance with the value of the capacitors C1 and C2, which are driven by the respective drivers 16 and 18. If C1 is chosen to be equal to $(\frac{2}{3})C$, and C2 is chosen to be equal to $(\frac{1}{3})C$, then if only C1 is driven, $V_0$ equals $(\frac{2}{3})V_{max}$.

In generalized terms, if $C_D$ represents the capacitance value of the capacitors driven, that is those capacitors to which the source 34 causes the capacitors to be periodically coupled and decoupled to the source V in accordance with the signal frequency of source 34, then the voltage $V_0$ may be determined by the equation $$V_0 = V_{max} \times \frac{C_D}{C}$$

Alternately, C1 may be equated to K C and C2 therefore to $(1-K)C$, with K less than 1, such that the values of C1 and C2 may readily be calculated once the desired output voltage levels or ratios thereof are selected. Under the above capacitance value allocation, and with only C2 driven, $V_0$ equals $(\frac{1}{3})V_{max}$. A complete truth table is shown in FIG. 2, which includes the possible combinations of the CONTL signal logical state assignments and the corresponding value of $V_0$.

In accordance with the present invention, due to the driver load characteristics, that is, high inductance value and low resistance value for the inductor L and a relatively lossless capacitor C, the circuit has a high "Q" value manifesting in a substantially lossless load, having an output signal comprising a fundamental and essentially no appreciable harmonics. Moreover, since the circuit maintains a constant capacitance value, the output frequency is maintained at a constant value of $F_0$, independent of the number and identity of capacitors being driven.

The invention described herein, therefore, provides the adjustment of output level without the loss of efficiency, and without altering the power supply output voltage, or the use of the power-wasting series resistors.

What is claimed is:

1. An adjustable output level signal transmitter comprising:
   a direct current source of electrical energy;
   L-C tank circuit means for providing the adjustable output level signal, the direct current source of electrical energy and the L-C tank circuit means having a common ground; the L-C tank circuit means comprising inductor L and capacitor C, said capacitor C further comprising a plurality of capacitors;
   switch means disposed between the direct current source of electrical energy and each one of the plurality of capacitors of the L-C tank circuit means for electrically coupling and decoupling selected ones of the plurality of capacitors of the L-C tank circuit means and the direct current source of electrical energy for adjusting thereby the level of the adjustable output level signal; and
   means for controlling the switch means for electrically coupling and decoupling selected ones of the plurality of capacitors of the L-C tank circuit means and the direct current source of electrical energy at a predetermined frequency.

2. The adjustable output level signal transmitter of claim 1, wherein the L-C tank circuit means comprises:
   a first capacitor C1 having first and second terminals;
   a second capacitor C2 having first and second terminals, the capacitors C1 and C2 in series circuit connection with the second terminals of each capacitor connected together; and
   an inductor L coupled between the second terminals of the capacitors and ground, the adjustable output level signal available at the second terminals of the capacitors, the fundamental frequency of oscillation $F_0$ of the L-C tank circuit means being determined by the relationship $$F_0 = \frac{1}{2\pi\sqrt{LC}}$$

where $F_0$ is measured in cycles per second (hertz); capacitance equal to C1+C2; and L is the value of the inductance of the inductor L.

3. The adjustable output level signal transmitter of claim 2, wherein the switch means comprises:
at least one driver, the driver having a driver output and a driver input and a pair of complementary switches in series circuit connection between the direct current source of electrical energy and ground, each switch of the pair of complementary switches operation between open and closed conditions, such that when one switch of the pair is in the open condition, the other switch of the pair is in the closed condition, the point of connection of the complementary switches being coupled to the driver output, the condition of the complementary switches being a function of the driver input, such that when the driver input is at a first value, one switch of the pair is in the open condition wherein the drier output is coupled to ground, thereby decoupling the L-C tank circuit means from the direct current source of electrical energy, and when the driver input is at a second value, such switch is in the closed position wherein the driver output is coupled to the direct current source of electrical energy, and thereby coupling the L-C tank circuit means to the direct current source of electrical energy.

4. The adjustable output level signal transmitter of claim 3, wherein the switch means further comprises:
at least one driver control switch having an output coupled to the driver input of the at least one driver; and
inputs comprising:
a logic input signal, having at least first and second logic states,
a direct current signal source, and
an alternating current signal source, wherein when the first logic input signal is in the first logic state, the output of the driver control switch is coupled to the direct current signal source, and when the logic signal is in the second state, the output is coupled to the alternating current signal source.

5. The adjustable output level signal transmitter of claim 4, wherein the at least one driver comprises:
a pair of drivers and the at least one driver control switches comprises a pair of driver control switches, one of the driver control switches of the pair coupled to a respective one of the drivers, and wherein the first terminal of the first capacitor C1 is coupled to the output of one driver and the first terminal of the second capacitor C2 is coupled to the output of the other driver.

6. The adjustable output level signal transmitter of claim 5, wherein the at least one driver control switch comprises:
a pair of driver control switches, wherein the logic input signal comprises:
a first logic input signal coupled to one of the pair driver control switches, and
a second logic input signal coupled to the other one of the pair of driver control switches.

7. The adjustable output level signal transmitter of claim 6, wherein the alternating current signal source has a fundamental frequency substantially equal to $F_0$, and wherein the adjustable output level signal is substantially sinusoidal having a maximum magnitude equal to $V_{max}$.

8. The adjustable output level signal transmitter of claim 7, wherein:
the value of C1 is K·C and
the value of C2 is (1−K)·C
where K is a constant less than 1,
such that when the first and second logic input signals are in the first logic state, the magnitude of the adjustable output level signal is substantially equal to zero, and when the first and second logic input signals are in the second logic state, the magnitude of the adjustable output level signal is equal to $V_{max}$.

9. The adjustable output level signal transmitter of claim 8, wherein when the first logic input signal is in the first logic state and the second logic input signal is in the second logic state, the magnitude of the adjustable output level signal is equal to $K \cdot V_{max}$ and when the first logic input signal is in the second logic state and the second logic input signal is in the first logic state, the magnitude of the adjustable output level signal is equal to $(1-K) V_{max}$.

10. The adjustable output level signal transmitter of claim 9, wherein the alternating current signal source is a square wave signal having a 50% duty cycle.

11. An adjustable output level signal transmitter comprising:
a direct current source of electrical energy;
an L-C tank circuit providing the adjustable output level signal, the direct current source of electrical energy and the L-C tank circuit having a common ground, the L-C tank circuit having a fundamental frequency of oscillation which remains constant independent of the level of the adjustable output level signal, the L-C tank circuit comprising:
a first capacitor C1 having first and second terminals;
a second capacitor C2 having first and second terminals, the second terminals of each capacitor connected together; and
an inductor L coupled between the second terminals of the capacitors and ground, the adjustable output level signal available at the second terminals of the capacitors, the fundamental frequency of oscillation $F_0$ of the L-C tank circuit being determined by the relationship:

$$F_0 = \frac{1}{2\pi\sqrt{LC}}$$

where $F_0$ is measured in cycles per second (Hertz); C is the value of capacitance equal to the combined capacitance of C1+C2; and L is the value of the inductance of the inductor L,
switch means disposed between the direct current source of electrical energy and the first terminals of capacitor C1 and capacitor C2 of the L-C tank circuit for selectively coupling and decoupling capacitor C1 and capacitor C2 of the L-C tank circuit and the direct current source of electrical energy; and
means for controlling the switch means for electrically coupling and decoupling capacitor C1 and capacitor C2 of the L-C tank circuit and the direct current source of electrical energy at a predetermined frequency.

12. The adjustable output level signal transmitter of claim 11, wherein the switch means comprises:
   a pair of drivers, each driver having a driver output, the output of one driver coupled to the first terminal of capacitor C1 and the output of the other driver coupled to the first terminal of capacitor C2,
   a driver input and a pair of complementary switches in series circuit connection between the direct current source of electrical energy and ground, each switch of the pair of complementary switches operating between open and closed conditions, such that when one switch of the pair is in the open condition, the other switch of the pair is in the closed condition, the condition of the complementary switches being a function of the driver input, such that when the driver input is at a first value, one switch of the pair is in the open condition wherein the driver output is coupled to ground, thereby decoupling the L-C tank circuit from the direct current source of electrical energy, and when the driver input is at a second value, each switch is in the closed position wherein the driver output is coupled to the direct current source of electrical energy, and thereby coupling the L-C tank circuit means to the direct current source of electrical energy.

13. The adjustable output level signal transmitter of claim 12, wherein the switch means further comprises:
   a pair of driver control switches, each driver control switch having an output coupled to the input of respective ones of the drivers; and
   inputs comprising:
      a logic input signal, having at least first and second logic states,
      a direct current signal source, and
      an alternating current signal source, wherein when the first logic input signal is in the first logic state, the output of the respective driver control switch is coupled to the direct current signal source, and when the logic signal is in the second state, the respective driver control switch output is coupled to the alternating current signal source.

14. The adjustable output level signal transmitter of claim 13, wherein the logic input signal comprises:
   a first logic input signal coupled to one of the pair of driver control switches, and
   a second logic input signal coupled to the other one of the pair of driver control switches.

15. The adjustable output level signal transmitter of claim 14, wherein the alternating current signal source has a fundamental frequency substantially equal to $F_0$, and wherein the adjustable output level signal is substantially sinusoidal having maximum magnitude equal to $V_{max}$.

16. An adjustable output level signal transmitter comprising:
   a direct current source of electrical energy;
   an L-C tank circuit, the direct current source of electrical energy and the L-C tank circuit having a common ground, the L-C tank circuit comprising:
   a first capacitor C1 having first and second terminals;
   a second capacitor C2 having first and second terminals, the capacitors C1 and C2 in series circuit connection with the second terminals of each capacitor connected together; and
   an inductor L coupled between the second terminals of the capacitors and ground, the adjustable output level signal available at the second terminals of the capacitors, the fundamental frequency of oscillation $F_0$ of the L-C tank circuit being determined by the relationship:

$$F_0 = \frac{1}{2\pi \sqrt{LC}}$$

where $F_0$ is measured in cycles per second (hertz); C is the value of capacitance equal to the combined capacitance of C1+C2; and L is the value of the inductance of the inductor L,
   a separate driver coupled to each capacitor, each driver operable between two logical states for connecting each capacitor to the direct current source of electrical energy or to ground, depending on the state of the respective driver, such that the level of the output of the signal transmitter is adjustable to discrete values as a function of the logical states of the drivers, wherein the fundamental frequency of oscillation remains constant independent of the logical states of the drivers; and
   means for controlling the drivers for electrically coupling and decoupling the L-C tank circuit and the direct current source of electrical energy at a predetermined frequency.

17. An adjustable output level signal transmitter comprising:
   a direct current source of electrical energy;
   L-C tank circuit means having an inductor L and a capacitor C for providing the adjustable output level signal at a frequency determined as a function of the values of inductor L and capacitor C, the direct current source of electrical energy and the L-C tank circuit means having a common ground and wherein C comprises capacitors C1 and C2;
   a driver coupled between the direct current source of electrical energy and C1 and another driver coupled between the direct current source of electrical energy and C2; and
   means for controlling each of the drivers for electrically coupling and decoupling the respective capacitors and the direct current source of electrical energy at a predetermined frequency.

18. The adjustable output level signal transmitter of claim 17, wherein the value of the adjustable output level signal is a function of which of the capacitors are electrically coupled to or decoupled from the direct current source of electrical energy.

19. The adjustable output level signal transmitter of claim 18, wherein the adjustable output level signal has a maximum value of $V_{max}$ and wherein the value of C1 is K·C, where K is a constant having a value less than 1, the value of C2 is (1−K)·C, such that the adjustable output level signal has discrete values of $V_{max}$ or K·$V_{max}$ or (1−K) $V_{max}$ or 0, depending upon which of said capacitors C1 and C2 are coupled to or decoupled from the direct current source of electrical energy.

20. An adjustable output level signal transmitter comprising:
   a direct current source of electrical energy;
   L-C tank circuit means having an inductor L and a capacitor C for providing the adjustable output level signal at a frequency of oscillation determined by the values of inductor L and capacitor C, wherein C comprises a plurality of capacitors;

a plurality of drivers, a different one of the plurality of drivers coupled between the direct current source of electrical energy and a respective one of the plurality of capacitors; and means for controlling each one of the plurality of drivers for electrically coupling and decoupling the respective ones of the capacitors and the direct current source of electrical energy at a predetermined frequency.

21. The adjustable output level signal transmitter of claim 20, wherein the L-C tank circuit means has a fundamental frequency of oscillation which remains constant independent of the level of the adjustable output level signal.

* * * * *